United States Patent
Grady et al.

(10) Patent No.: US 11,862,342 B2
(45) Date of Patent: *Jan. 2, 2024

(54) SYSTEMS AND METHODS FOR EMBOLISM PREDICTION USING EMBOLUS SOURCE AND DESTINATION PROBABILITIES

(71) Applicant: HeartFlow, Inc., Redwood City, CA (US)

(72) Inventors: Leo J. Grady, Darien, CT (US); Gilwoo Choi, Mountain View, CA (US); Charles A. Taylor, Atherton, CA (US); Christopher K. Zarins, Austin, TX (US)

(73) Assignee: HeartFlow, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/184,769

(22) Filed: Mar. 16, 2023

(65) Prior Publication Data
US 2023/0223148 A1    Jul. 13, 2023

Related U.S. Application Data

(63) Continuation of application No. 16/727,161, filed on Dec. 26, 2019, now Pat. No. 11,646,118, which is a
(Continued)

(51) Int. Cl.
*G16H 50/20* (2018.01)
*G16H 50/50* (2018.01)
(Continued)

(52) U.S. Cl.
CPC ............. *G16H 50/20* (2018.01); *A61B 34/10* (2016.02); *G06F 17/18* (2013.01); *G06N 7/01* (2023.01);
(Continued)

(58) Field of Classification Search
CPC ..... G06F 19/3437; G06F 17/18; G06N 1/005; G16H 50/20
See application file for complete search history.

(56) References Cited

U.S. PATENT DOCUMENTS 8,315,812 B2    11/2012    Taylor
2012/0041318 A1    2/2012    Taylor
(Continued)

FOREIGN PATENT DOCUMENTS

WO    2013071219 A1    5/2013

OTHER PUBLICATIONS

Fabbri, Dario, et al. "Computational modeling of emboli travel trajectories in cerebral arteries: influence of microembolic particle size and density." Biomechanics and modeling in mechanobiology 13.2 (2014): 289-302.
(Continued)

*Primary Examiner* — Vincent Rudolph
*Assistant Examiner* — Raphael Schwartz
(74) *Attorney, Agent, or Firm* — Bookoff McAndrews, PLLC

(57) ABSTRACT

Systems and methods are disclosed for determining a patient risk assessment or treatment plan based on emboli dislodgement and destination. One method includes receiving a patient-specific anatomic model generated from patient-specific imaging of at least a portion of a patient's vasculature; determining or receiving a location of interest in the patient-specific anatomic model of the patient's vasculature; using a computing processor for calculating blood flow through the patient-specific anatomic model to determine blood flow characteristics through at least the portion of the patient's vasculature of the patient-specific anatomic model downstream from the location of interest; and using a computing processor for particle tracking through the simu-
(Continued)

lated blood flow to determine a destination probability of an embolus originating from the location of interest in the patient-specific anatomic model, based on the determined blood flow characteristics.

20 Claims, 12 Drawing Sheets

Related U.S. Application Data continuation of application No. 15/827,725, filed on Nov. 30, 2017, now Pat. No. 10,553,317, which is a continuation of application No. 15/093,985, filed on Apr. 8, 2016, now Pat. No. 9,864,840, which is a continuation of application No. 14/994,365, filed on Jan. 13, 2016, now abandoned.

(60) Provisional application No. 62/103,230, filed on Jan. 14, 2015.

(51) Int. Cl.
*G06N 7/01* (2023.01)
*A61B 34/10* (2016.01)
*G16H 50/30* (2018.01)
*G06F 17/18* (2006.01)

(52) U.S. Cl.
CPC .............. *G16H 50/30* (2018.01); *G16H 50/50* (2018.01); *A61B 2034/105* (2016.02); *A61B 2034/107* (2016.02)

(56) References Cited

U.S. PATENT DOCUMENTS

2012/0041739 A1 2/2012 Taylor
2014/0073976 A1 3/2014 Fonte et al.

OTHER PUBLICATIONS

I. A. Carr et al.: "Size-dependent predilections of cardiogenic embolic transport", American Journal of Physiology: Heart and Circulatory Physiology, vol. 305, No. 5, Jun. 21, 2013 (Jun. 21, 2013), pp. H732-H739.

International Search Report and Written Opinion for corresponding Application No. PCT/US2016/013165 dated Apr. 28, 2016, (14 pages).

Linear Classifier, Wikipedia, the free encyclopedia, Jun. 5, 2013, https://en.wikipedia.org/w/index.php?title=Linear_classifier&oldid=558432237 (Year: 2013).

Platt, Allan. "Can you recognize a patient at risk for a hypercoagulable state?." Journal of the American Academy of Physician Assistants 21.12 (2008): 20-26.

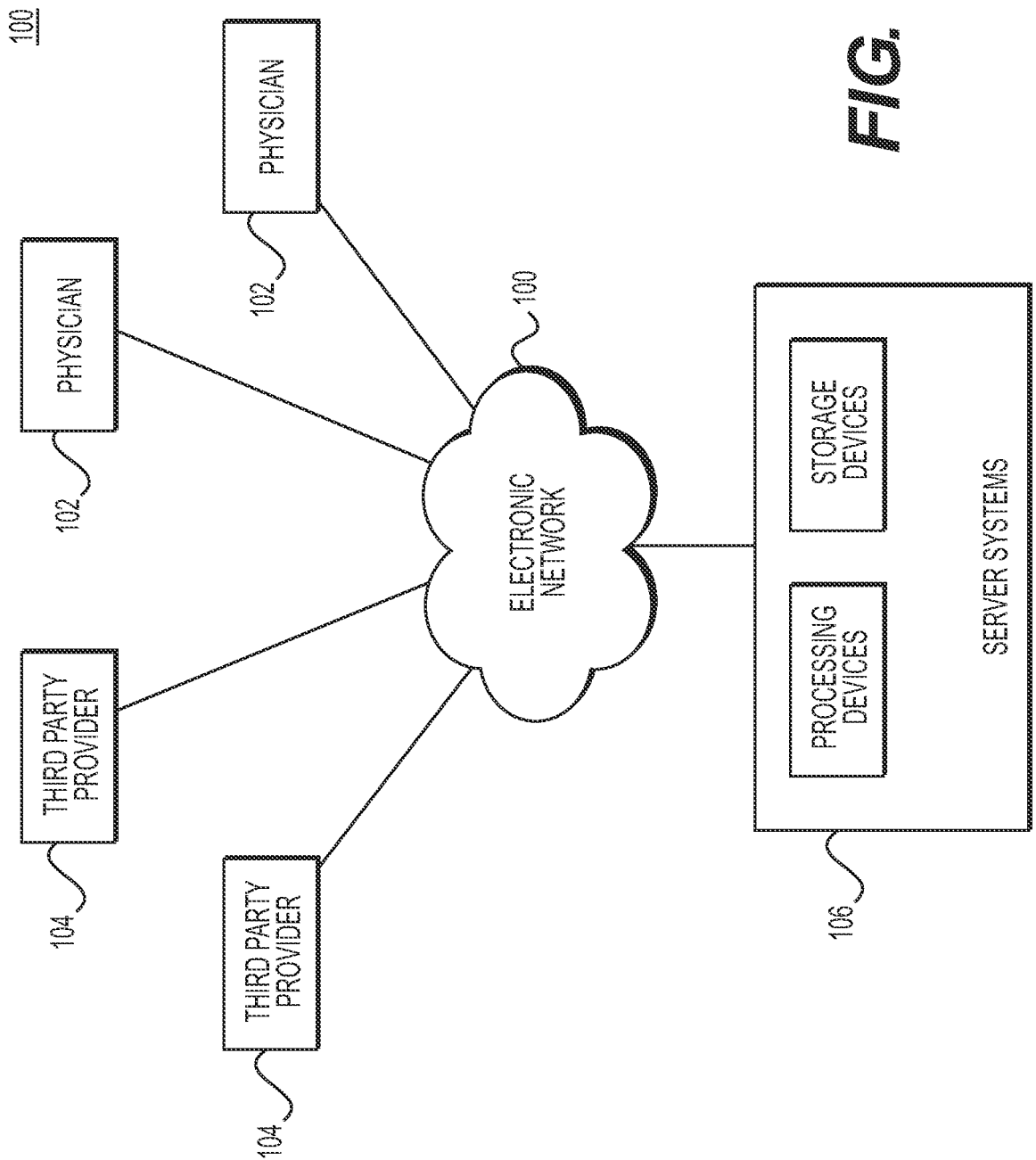

SYSTEMS AND METHODS FOR EMBOLISM PREDICTION USING EMBOLUS SOURCE AND DESTINATION PROBABILITIES

RELATED APPLICATION(S)

This application is a continuation of U.S. patent application Ser. No. 16/727,161, filed Dec. 26, 2019, which is a continuation of U.S. patent application Ser. No. 15/827,725, filed Nov. 30, 2017, now U.S. Pat. No. 10,553,317, which is a continuation of U.S. patent application Ser. No. 15/093,985, filed Apr. 8, 2016, now U.S. Pat. No. 9,864,840, which is a continuation of U.S. patent application Ser. No. 14/994,365, filed Jan. 13, 2016, now abandoned, which claims priority to U.S. Provisional Application No. 62/103,230 filed Jan. 14, 2015, all of which are incorporated herein by reference in their entireties.

FIELD OF THE DISCLOSURE

Various embodiments of the present disclosure relate generally to disease assessment and related methods. More specifically, particular embodiments of the present disclosure relate to systems and methods for disease assessment using predictions regarding embolism dislodgement and destination.

BACKGROUND

Emboli are intravascular masses that travel through the bloodstream. Clinical consequences may occur when an embolus lodges in a blood vessel, causing a blockage of the vessel and obstructing blood flow. The level of harm introduced by an embolism may be related to the location in the patient's vasculature where an embolus lodged. In other words, an embolus destination may determine the impact of that embolus on a patient's health. For example, a sizable embolus entering the lungs may cause a life-threatening pulmonary embolism. An embolus lodging in the brain may cause a stroke. By contrast, emboli entering vessels in muscles or the liver may have less impact on a patient's body.

Thus, a desire exists to better predict embolus destination, or locations in a vasculature that may be vulnerable to an embolism lodging at that location. By better understanding emboli destinations, practitioners may better predict the degree of harm that the emboli may inflict on a patient. Meanwhile, a desire also exists for identifying source locations of emboli causing harmful embolisms, so that treatments may be targeted at those source locations.

The foregoing general description and the following detailed description are directed to overcoming one or more of the challenges described above. The general description and detailed description are exemplary and explanatory only and are not restrictive of the disclosure.

SUMMARY

According to certain aspects of the present disclosure, systems and methods are disclosed for disease assessment using predictions regarding embolism dislodgement and destination.

One method includes: receiving a patient-specific anatomic model generated from patient-specific imaging of at least a portion of a patient's vasculature; determining or receiving a location of interest in the patient-specific anatomic model of the patient's vasculature; using a computing processor for calculating blood flow through the patient-specific anatomic model to determine blood flow characteristics through at least the portion of the patient's vasculature of the patient-specific anatomic model downstream from the location of interest; and using a computing processor for particle tracking through the simulated blood flow to determine a destination probability of an embolus originating from the location of interest in the patient-specific anatomic model, based on the determined blood flow characteristics.

In accordance with another embodiment, a system is disclosed for determining a patient risk assessment or treatment plan based on emboli dislodgement and destination: a data storage device storing instructions for simulating or optimizing hemodialysis access; and a processor configured for: receiving a patient-specific anatomic model generated from patient-specific imaging of at least a portion of a patient's vasculature; determining or receiving a location of interest in the patient-specific anatomic model of the patient's vasculature; using a computing processor for calculating blood flow through the patient-specific anatomic model to determine blood flow characteristics through at least the portion of the patient's vasculature of the patient-specific anatomic model downstream from the location of interest; and using a computing processor for particle tracking through the simulated blood flow to determine a destination probability of an embolus originating from the location of interest in the patient-specific anatomic model, based on the determined blood flow characteristics.

In accordance with another embodiment, a non-transitory computer readable medium is disclosed for use on a computer system containing computer-executable programming instructions for performing a method of determining a patient risk assessment or treatment plan based on emboli dislodgement and destination, the method comprising: receiving a patient-specific anatomic model generated from patient-specific imaging of at least a portion of a patient's vasculature; determining or receiving a location of interest in the patient-specific anatomic model of the patient's vasculature; using a computing processor for calculating blood flow through the patient-specific anatomic model to determine blood flow characteristics through at least the portion of the patient's vasculature of the patient-specific anatomic model downstream from the location of interest; and using a computing processor for particle tracking through the simulated blood flow to determine a destination probability of an embolus originating from the location of interest in the patient-specific anatomic model, based on the determined blood flow characteristics.

Another method includes: receiving a patient-specific anatomic model of at least a portion of a patient's vasculature; determining or receiving a destination location of interest in the patient-specific anatomic model, wherein the destination location of interest is an embolus destination or an embolism location in the patient's vasculature; determining a destination probability of an embolus in the patient's vasculature lodging at the destination location of interest; and determining a source of the embolus in the patient's vasculature, based on the destination probability of the embolus.

Yet another method includes: receiving a patient-specific anatomic model of a patient's vasculature; receiving an anatomic location associated with a vascular treatment or a vascular procedure; determining or receiving one or more blood flow characteristics through the anatomic location associated with the vascular treatment or the vascular procedure; determining a destination probability of an embolus traveling through the patient's vasculature, based on the one or more determined blood flow characteristics through the anatomic location associated with the vascular treatment or the vascular procedure; and determining a vulnerable embolism location in the patient's vasculature based on the determined destination probability.

Yet another method includes: receiving a medical condition or disease of interest; determining a vessel associated with causing the medical condition or disease of interest; determining a probability of an embolus lodging in the vessel associated with causing the medical condition or disease of interest, where the probability is computed or retrieved from a database; and determining a vascular source of the embolus, based on the probability of the embolus lodging in the vessel associated with causing the medical condition or disease of interest.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 1 is a block diagram of an exemplary system and network for disease assessment using predictions regarding embolism dislodgement and destination, according to an exemplary embodiment of the present disclosure.

DESCRIPTION OF THE EMBODIMENTS

Figure 2A:
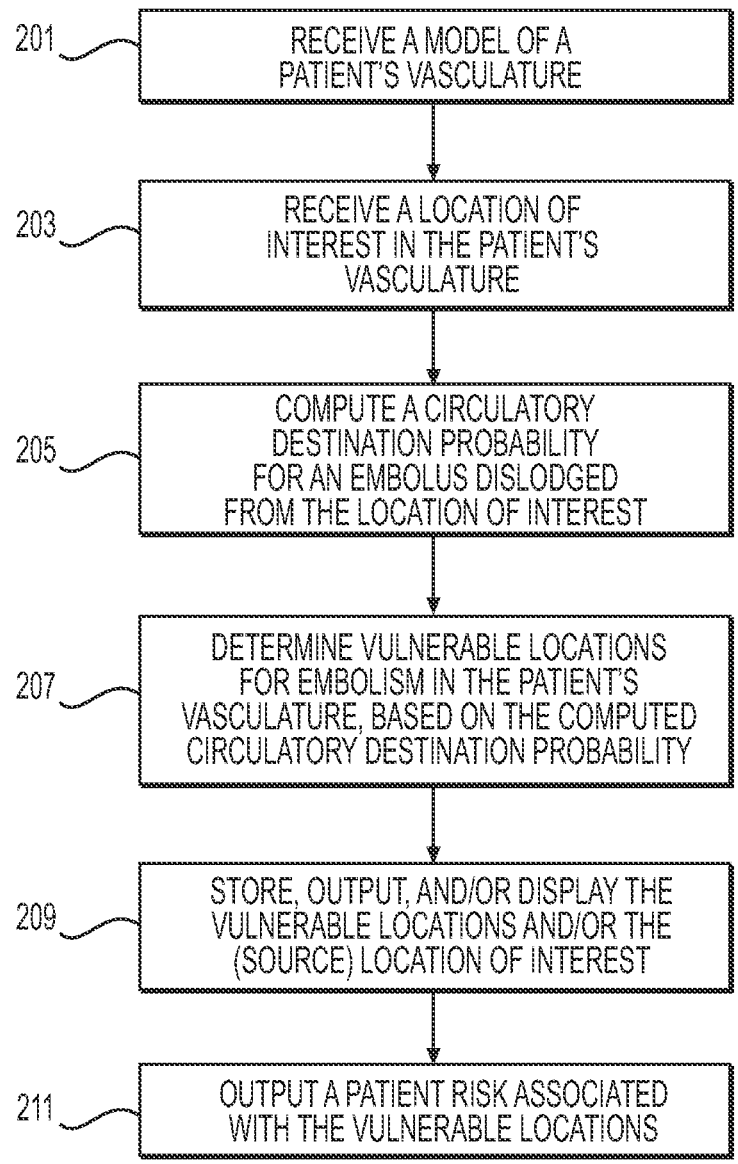
FIG. 2A is a flowchart of an exemplary method of determining emboli circulatory destination probabilities, according to an exemplary embodiment of the present disclosure.

Reference will now be made in detail to the exemplary embodiments of the disclosure, examples of which are illustrated in the accompanying drawings. Wherever possible, the same reference numbers will be used throughout the drawings to refer to the same or like parts.

An embolus dislodged from atherosclerotic plaques may cause clinical complications, depending on the source and destination of the embolus in the circulatory system. In other words, patient risk of heart disease and attack may be based, in part, on embolus destination, e.g., in the coronary arteries. The size and destination of an embolus may indicate the extent to which the embolus may harm the patient. For example, deep vein thrombosis may cause a life-threatening pulmonary embolism if a sizable embolus enters the lungs. As another example, embolism in patients may cause stroke or transient ischemic attack (TIA). Similarly, early microembolism after carotid endarterectomy may relate to postoperative cerebral ischemia. Stroke may also be caused by embolization from the aortic arch or other places in the vasculature, including the left atrial appendage of the heart. Thus, a desire exists to better predict embolus destination. The present disclosure includes methods to determine embolus destination based on the location of embolic source, vascular anatomy, blood flow characteristics, and/or circulatory system.

This disclosure includes systems and methods for assessing the impact of an embolus, as a function of the source of the embolus and a patient's circulatory system. For example, this disclosure describes systems and methods for predicting the circulatory destination probability of an embolus dislodged from a specified location, including the heart (e.g., left atrium, left atrium with atrial fibrillation, aortic valve, mitral valve, left ventricular aneurysms, prosthetic aortic or mitral valves, abdominal aorta, carotid, coronary arteries, veins, etc.) to assess (i) the impact of an embolus on cerebral-related risks (e.g., cognitive impairment, stroke, TIA), (ii) the impact of an embolus on peripheral-related risks (e.g., pulmonary embolism), and/or (iii) a risk of potential emboli dislodgement associated with invasive procedures.

Thus, this disclosure includes systems and methods for assessing the impact of embolism on patient risk and evaluating therapeutic options based, at least in part, on the impact of embolism. The disclosure further includes systems and methods for evaluating therapeutic options based on the assessments. For example, this disclosure may include methods to identify culprit embolic sources for treatment. Identifying or predicting source locations of emboli may provide treatment recommendations targeted to locations where dislodged emboli may cause a harmful embolism.

Referring now to the figures, FIG. 1 depicts a block diagram of an exemplary system 100 and network for disease assessment using predictions regarding embolism dislodgement and destination, according to an exemplary embodiment. Specifically, FIG. 1 depicts a plurality of physicians 102 and third party providers 104, any of whom may be connected to an electronic network 101, for example, the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, including age, medical history, blood pressure, blood viscosity, patient activity or exercise level, etc. Physicians 102 and/or third party providers 104 may transmit the anatomical images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices. For the present disclosure, "patient" may refer to any individual of interest.

Figure 2B:
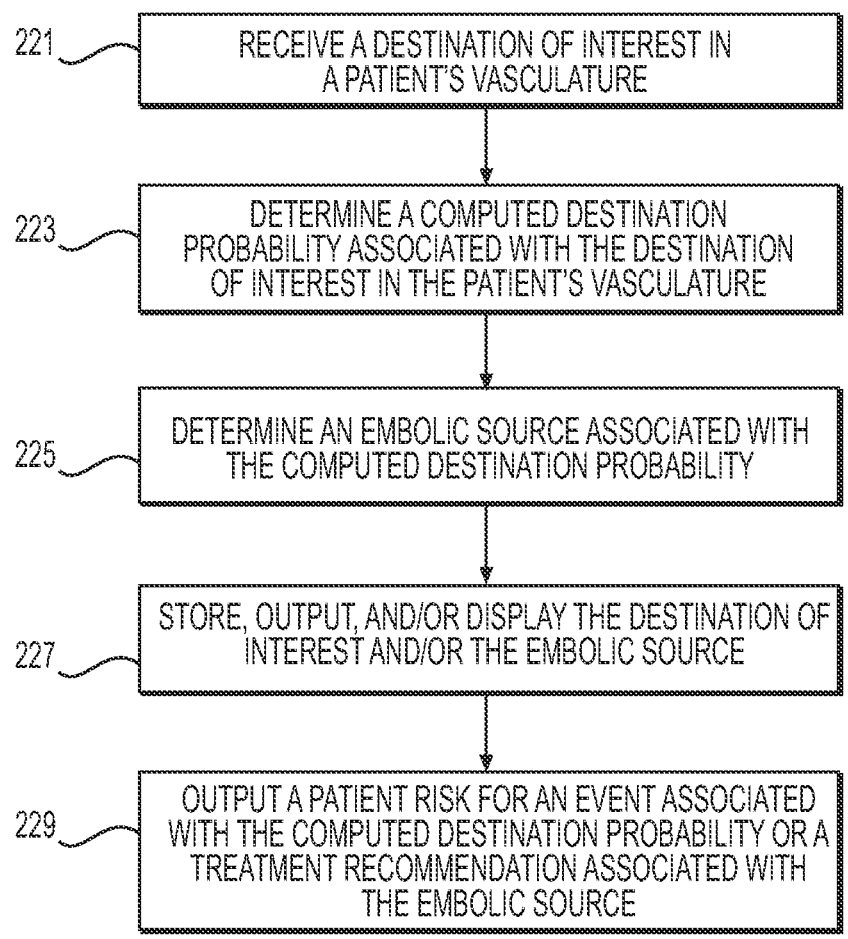
FIG. 2B is a flowchart of an exemplary method of identifying source locations for emboli, according to an exemplary embodiment of the present disclosure.
Figure 3A:
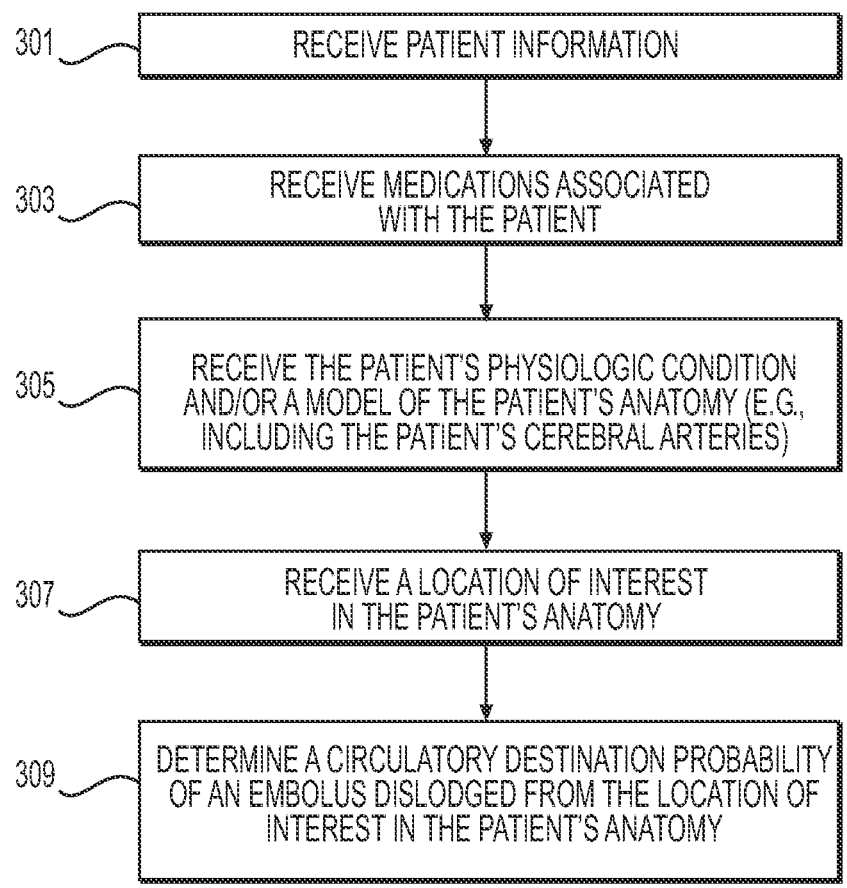
FIG. 3A is a flowchart of an exemplary method of determining destination(s) in cerebral vessels for an embolus dislodged from a location in a patient's vasculature, according to an exemplary embodiment of the present disclosure.
Figure 3B:
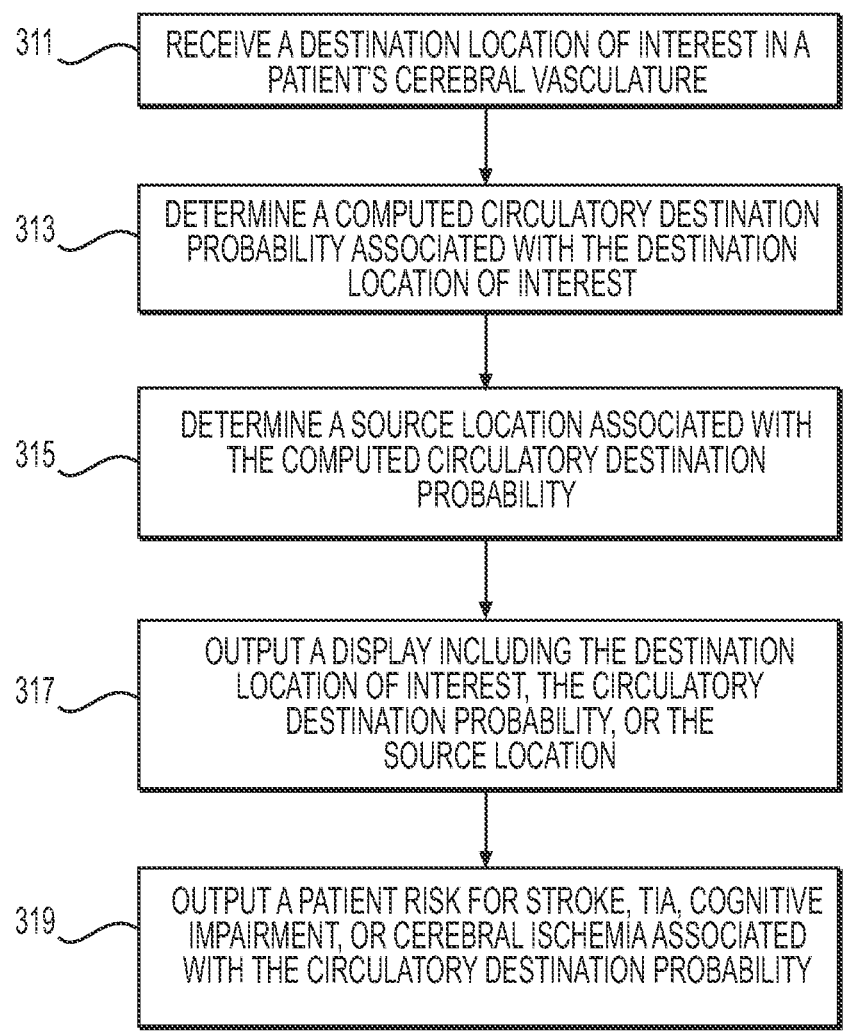
FIG. 3B is a flowchart of an exemplary method of determining and evaluating source locations of embolisms in a patient's cerebral vasculature, according to an exemplary embodiment of the present disclosure.
Figure 3C:
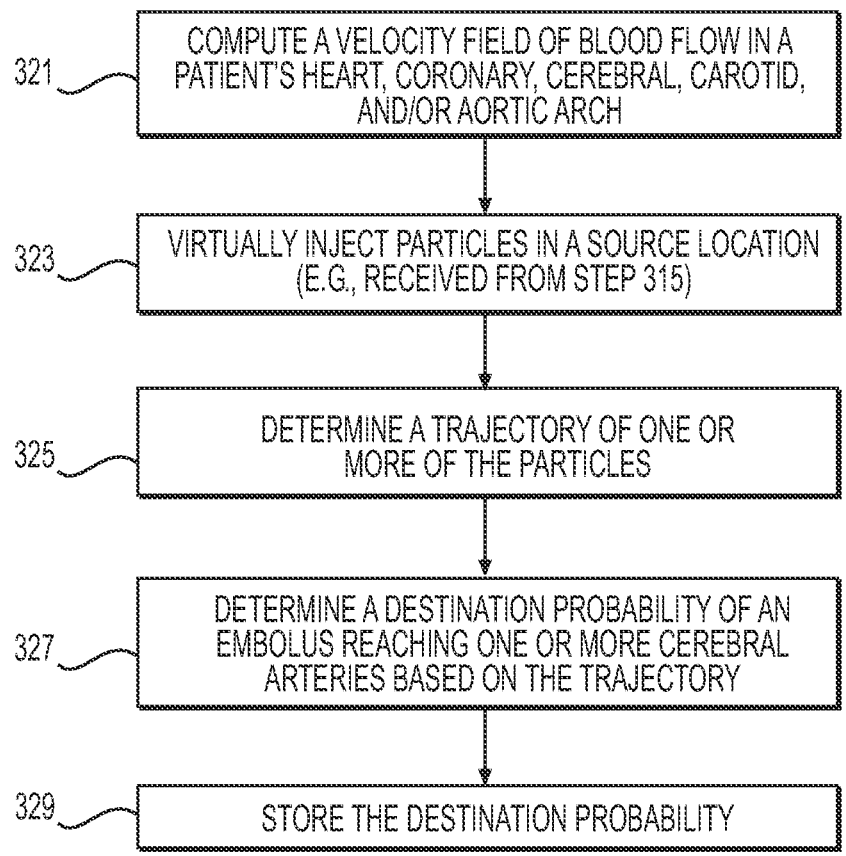
FIG. 3C is a flowchart of an exemplary method of determining blood flow characteristics to compute a circulatory destination probability of a dislodged embolus for cerebral-related risks, according to an exemplary embodiment of the present disclosure.
Figure 4A:
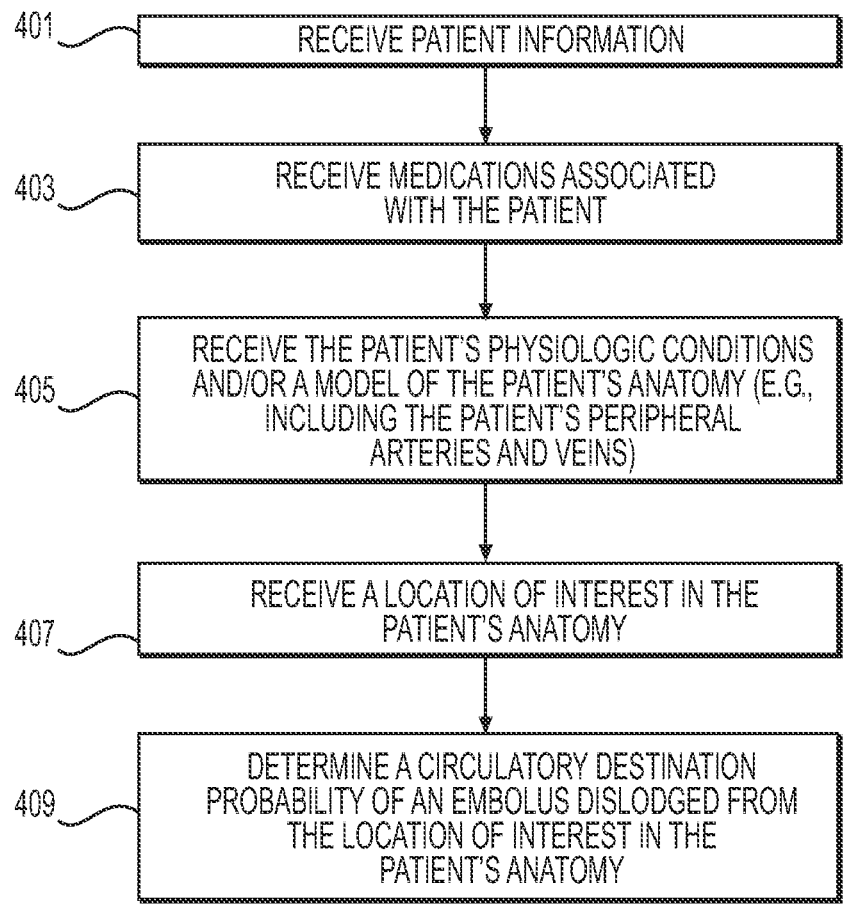
FIG. 4A is a flowchart of an exemplary method of determining destination(s) in peripheral vessels for an embolus dislodged from a location in a patient's vasculature, according to an exemplary embodiment of the present disclosure.
Figure 4B:
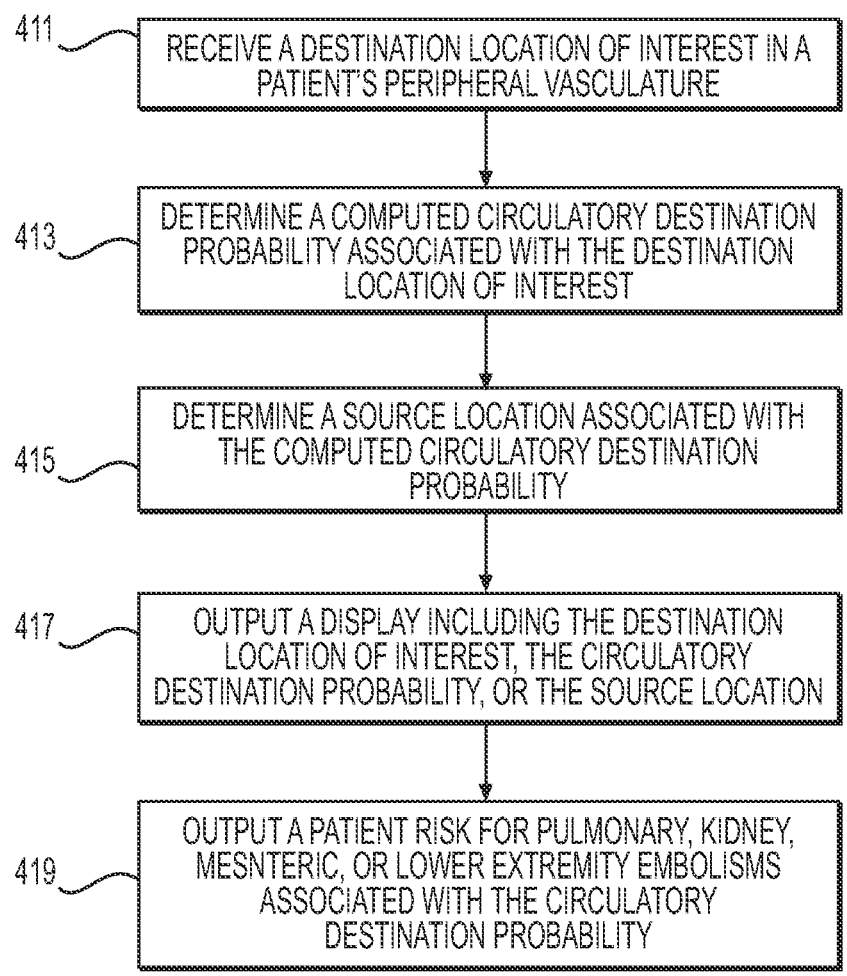
FIG. 4B is a flowchart of an exemplary method of determining and evaluating source locations of embolisms in a patient's peripheral vasculature, according to an exemplary embodiment of the present disclosure.
Figure 4C:
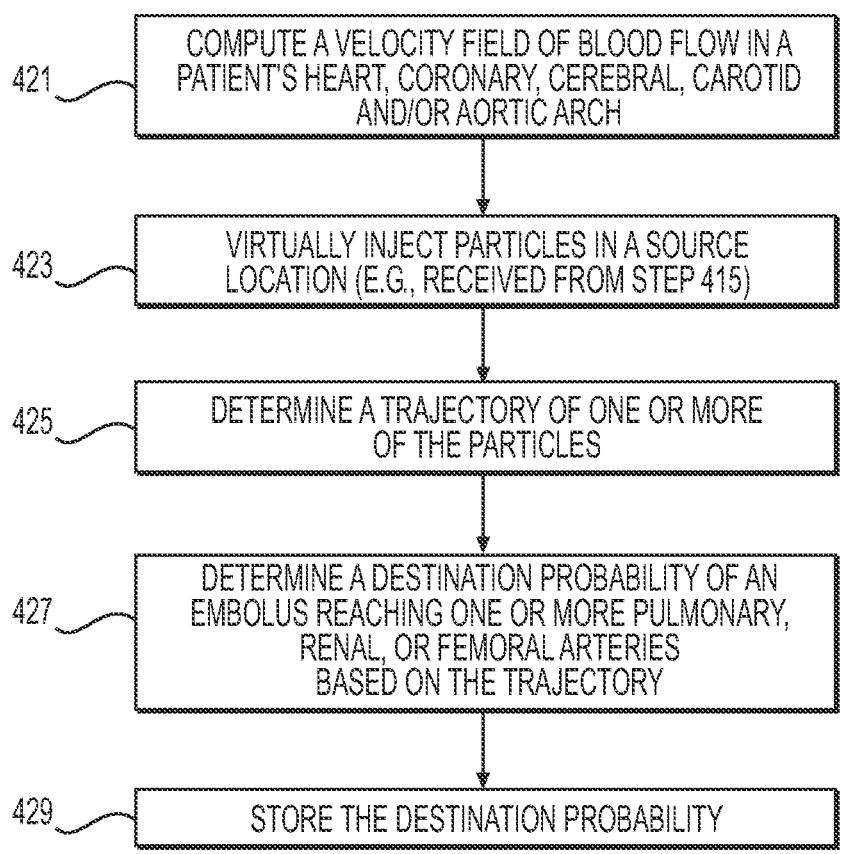
FIG. 4C is a flowchart of an exemplary method of determining blood flow characteristics and circulatory destination probability of a dislodged embolus for peripheral-related risks, according to an exemplary embodiment of the present disclosure.
Figure 5A:
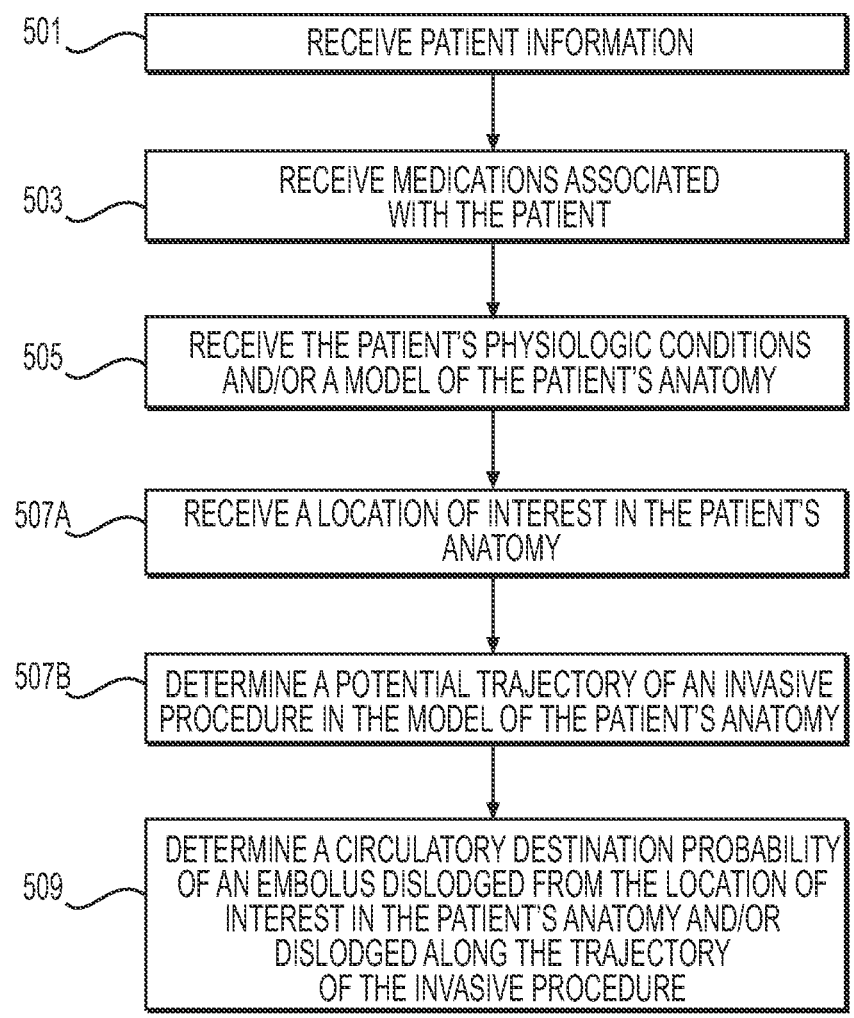
FIG. 5A is a flowchart of an exemplary method of assessing or assigning a risk of potential emboli dislodgement associated with an invasive procedure, according to an exemplary embodiment of the present disclosure.
Figure 5B:
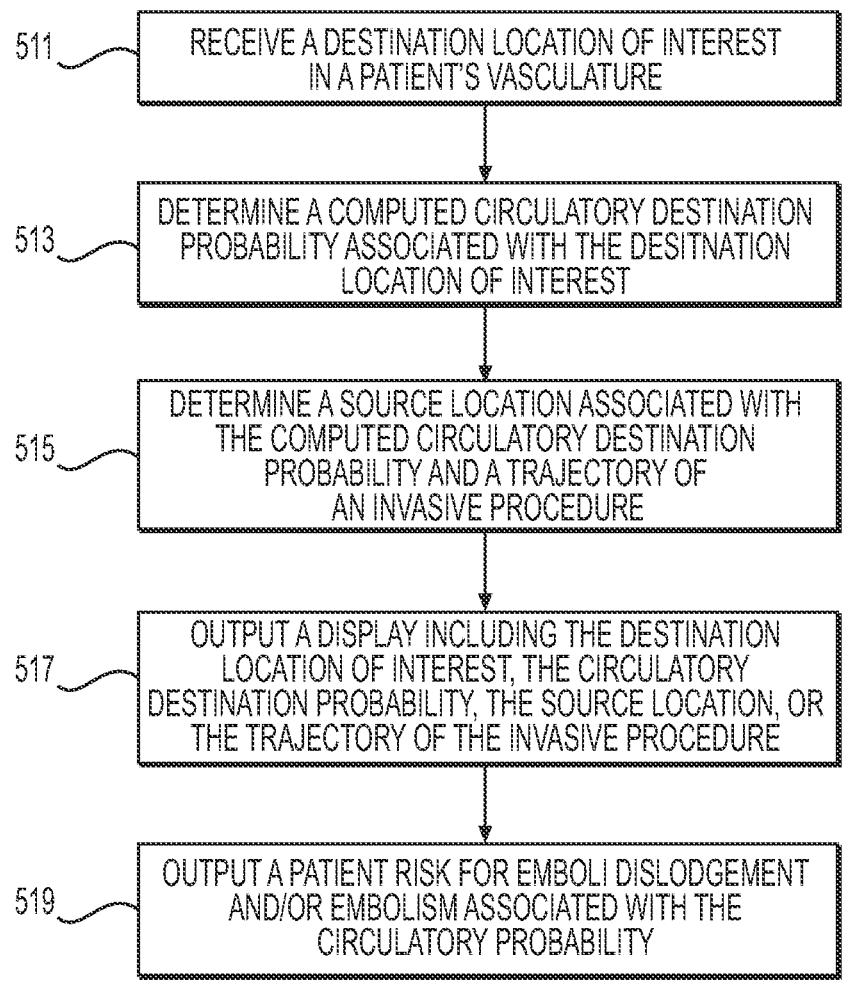
FIG. 5B is a flowchart of an exemplary method of determining and evaluating source locations of embolisms associated with invasive procedures, according to an exemplary embodiment of the present disclosure.
Figure 5C:
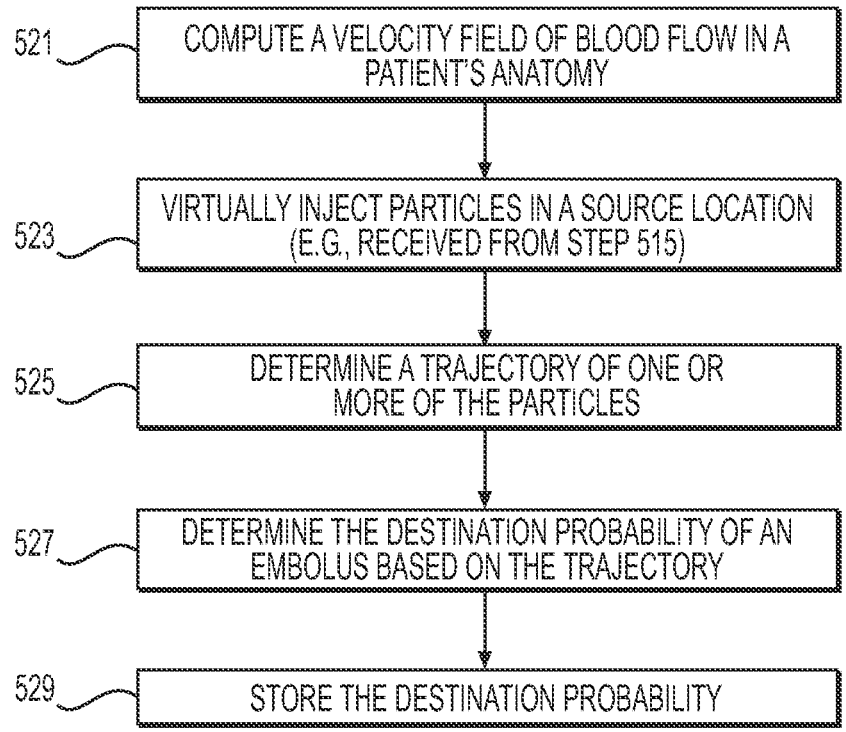
FIG. 5C is a flowchart of an exemplary method of determining blood flow characteristics to compute circulatory destination probability of a dislodged embolus related to invasive procedures, according to an exemplary embodiment of the present disclosure.

FIG. 2A depicts a flowchart of a general embodiment for identifying emboli source locations, circulatory destination probabilities, and locations vulnerable to embolism. The flowchart of FIG. 2A may further depict evaluating patient risk or treatment options associated with the circulatory destination probabilities and locations vulnerable to embolism. FIG. 2B depicts a flowchart of a general embodiment for finding embolic sources for one or more patient conditions or risks. FIGS. 3A-5B depict exemplary applications of the methods shown in FIGS. 2A and 2B. For example, FIGS. 3A-3C depict flowcharts for a specific embodiment for predicting cerebral-related risks and evaluating treatment options associated with the cerebral-related risks. FIGS. 4A-4C depict flowcharts for a specific embodiment for predicting peripheral-related risks and evaluating treatment options associated with the peripheral-related risks. FIGS. 5A-5C depict flowcharts for a specific embodiment for assessing a risks (e.g., of potential emboli dislodgement or embolism) associated with an invasive procedure. The exemplary methods of the figures may be performed or used individually, or in any combination. Any or all the steps of the exemplary methods may be performed using a computing processor.

FIG. 2A is a flowchart of an exemplary method 200 of determining emboli source locations, circulatory destination probabilities, and vessel locations vulnerable to embolism, according to an exemplary embodiment. The method of FIG. 2A may be performed by server systems 106, based on information, images, and data received from physicians 102 and/or third party providers 104 over electronic network 101.

In one embodiment, step 201 may include receiving a model of a patient's vasculature and physiologic characteristics (e.g., in an electronic storage medium). For example, the vascular model may include a portion of the patient's vasculature, or the patient's entire circulatory system. Various portions of the vascular model may be at imaged and/or modeled varying levels of detail. For example, in a case involving a model of the patient's entire circulatory system, prioritized portions or portions of interest in the patient's circulatory system may be modeled in greater detail. Remaining portions of the model may be inferred. One such exemplary scenario may include modeling portions of interest for the received patient vascular model as 3D geometric, anatomic models while modeling remaining portions of the received patient vascular model as reduced order models. The vascular model may include a composite of various models, reflecting, for instance, variations in geometry, psychological response, boundary conditions, and/or physics-based variations in blood flow for respective location(s) in the vasculature.

In one embodiment, step 203 may include receiving one or more locations of interest in the patient (e.g., a plaque, pathological area, location of possible vascular shedding, etc.) via invasive and/or noninvasive imaging, for storage in an electronic storage medium. Step 203 may also include identifying one or more locations of interest using a computing processor. For example, step 203 may include identifying a plaque, a pathological area, and/or a location of possible vascular shedding in the received model of the patient's vasculature and designating the identified plaque, pathological area, and/or location of possible vascular shedding as one or more locations of interest. In one embodiment, the one or more locations of interest may be stored within an electronic storage drive.

In one embodiment, step 205 may include computing circulatory destination probability in order to determine potential destination(s) for an embolus dislodged from one or more locations of interest. For example, step 205 may include determining one or more blood flow characteristics and using the determined blood flow characteristic(s) to determine the circulatory destination probability of an embolus dislodged from the identified locations of interest of the patient's vasculature. The blood flow characteristics may be determined based on the patient's vasculature and the received physiologic characteristics (e.g., from step 201). For example, the blood flow characteristics may be determined by simulating blood flow through at least a portion of the model of the patient's vasculature. The determinations of circulatory destination probability may be calculated via particle tracking, using a computing processor (as described in further detail, for example, at step 309 of FIG. 3A, step 409 of FIG. 4A, and step 509 of FIG. 5A).

In one embodiment, step 207 may include determining locations vulnerable to embolism, based on the computed destination probabilities for a given location in the patient's modeled vasculature (e.g., a location of interest). The circulatory destination probability may indicate a destination/target location in the patient's vasculature where the dislodged embolus (e.g., from step 203) may lodge, as well as the likelihood that the dislodged embolus would lodge at that particular destination. In other words, the output of step 207 may include various locations (e.g., destinations) in a patient's vasculature where an embolism may form, given the identified locations of interest (e.g., of step 203). In one embodiment, the various locations may comprise locations vulnerable to embolism (e.g., vulnerable locations in a patient's vasculature).

In a further embodiment, step 207 may include ranking or selecting locations vulnerable to embolism, from the various locations (e.g., destinations) in a patient's vasculature where an embolism may form. For example, step 207 may include identifying a location vulnerable in a patient's vasculature vulnerable to embolism where the destination probability of the location exceeds a predetermined threshold. Step 207 may include identifying a threshold destination probability of a location in the patient's vasculature. As an example, step 207 may designate a destination probability of 50% as a threshold, such that a destination probability that exceeds 50% may cause an associated location to be identified as a "vulnerable location." For instance, location A may be associated with a 56% likelihood of embolism, while location B may be associated with a 30% likelihood of embolism. Step 207 may include designating location A as a "vulnerable location" while location B is not. Alternately or in addition, vulnerable locations may be designated as locations in a vessel most vulnerable to embolism or with the highest likelihoods of embolism. For example, the three locations in a vessel most vulnerable to embolism or locations of a patient's vasculature with the top three destination probabilities may be designated as "vulnerable locations."

In one embodiment, step 207 may further include associating an identified vulnerable location (of embolism) with the location of interest (e.g., source location for the dislodged emboli). In other words, step 207 may further include determining, for a location in a patient's vasculature (e.g., an embolic source), a probability of embolism associated with emboli dislodging from the location.

In one embodiment, step 209 may include storing, outputting, and/or generating a representation of vulnerable embolism locations and associated embolic sources, e.g., to an electronic storage medium. In a further embodiment, step 211 may include outputting a patient risk of an event associated with the computed risk of embolism and/or the determined vulnerable embolism location(s). For example, computing patient risk for the event of a stroke may include one or more of the following: imaging at least a portion of the patient's aortic arch, great vessels, carotid artery, vertebral, and/or intracranial circulation, identifying, e.g., from imaging, plaques (e.g., at a carotid bifurcation), assessing a degree of stenosis, assessing plaque characteristics, assessing plaque composition, determining an association between a risk of stroke and a location of stroke (e.g., from an embolus). A risk of stroke and/or location of stroke (embolus) may be calculated by correlating risk to actual occurrences of stroke/TIA, diffusion weighted maps of MRI (e.g., to identify symptomatic stroke and areas of ischemia/infarction of a brain (that could be asymptomatic), etc.), etc. In another embodiment, computing patient risk for stroke may include calculating blood flow patterns and/or predicting vulnerable locations in a patient's anatomy for embolism/stroke.

Machine learning of plaque severity and/or location in conjunction with distribution of stroke (e.g., from MRI and head CTA) may enhance predictive certainty. In some cases, patient risk of an embolism-related event may be inferred from the risk of an embolism. In one embodiment, step 211 may include estimating the patient risk of an embolism-related event using a machine-learning based prediction model derived from clinical data on the relationship between detected emboli and actual clinical events. For instance, an exemplary event associated with the risk of embolism may include stroke. A vulnerable embolism location within the brain may relate to a high patient risk of stroke, whereas a patient may have a low risk of stroke if the computed circulatory destination probability indicates a low probability that an emboli from the patient's location of interest (e.g., from step 203), would lodge in the patient's cerebral vasculature.

In one embodiment, method 200 may include determining one or more destinations of interest (e.g., target location(s)) in the patient's vasculature. For example, destinations of interest may include locations in the circulatory system where embolism presence would be particularly harmful, e.g., one or more of the aorta, carotid artery, various peripheral vessels, etc. Determining the destinations of interest may include receiving and/or identifying the destinations of interest. Then, method 200 may include calculating a circulatory destination probability, in particular, for an embolus dislodged from a location of interest and traveling to one of the one or more destinations of interest. Such an embodiment may include an analysis in method 200 particularly providing determinations of risk of certain events associated with embolism. For example, a patient's lungs or the brain may serve as destinations of interest in a case where peripheral vessels (e.g., peripheral veins) may be defined as sources of interest and method 200 may be used to provide an assessment destination risk for embolization to the lungs (pulmonary embolism) or to the brain (if the patient has a patent foramen ovale in the heart). Then, method 200 may include calculating source probability of the peripheral vessels, destination probability of the lungs and brain, and/or the patient's risk of pulmonary embolism, rather than performing a more comprehensive assessment for several locations vulnerable to embolism or for patient risk of various different events associated with embolism.

FIG. 2B is a flowchart of an exemplary method 220 of identifying source locations for emboli, according to an exemplary embodiment. The method of FIG. 2B may be performed by server systems 106, based on information, images, and data received from physicians 102 and/or third party providers 104 over electronic network 101.

In one embodiment, step 221 may include receiving (and/or determining) one or more destinations of interest in a patient's vasculature. A destination of interest in a patient's vasculature may relate to a location in a patient's vasculature where an embolism may impact a patient's health, or create a risk of harm to the patient.

In one embodiment, step 223 may include determining a computed destination probability (e.g., from step 205 of method 200) associated with at least one destination of interest of the one or more destinations of interest. For example, step 223 may include retrieving, from stored destination probabilities (e.g., from step 209 of method 200), a destination probability associated with the at least one destination of interest. In some cases, multiple destination probabilities may be associated with a destination of interest, since emboli may be associated with various sources, each corresponding to a different destination probability.

In one embodiment, step 225 may include determining an embolic source associated with the computed destination probability (e.g., from step 205 or step 223) for the at least one destination of interest of the one or more destinations of interest of step 221. The embolic source may include a location in the model of the patient's vasculature comprising at least one location (or a portion of at least one location) of the one or more of the locations of interest (e.g., from step 203). For example, a location of interest may include a segment of the patient's modeled vasculature. The embolic source may include a particular location or sub-section of the segment of the patient's modeled vasculature. For example, emboli that may theoretically lodge at the destination of interest may arrive from several source locations within the patient's vasculature. Step 225 may include determining sources of emboli most likely to arrive at a destination of interest, given the patient's circulatory pattern.

In one embodiment, step 227 may include storing, outputting, and/or generating a representation of a destination of interest (e.g., a vulnerable embolism location) with one or more associated embolic sources, e.g., to an electronic storage medium.

In a further embodiment, step 229 may include outputting a patient risk of an event associated with a risk of embolism from the computed destination probability. Step 229 may further include generating treatment recommendations associated with one or more of the determined embolic sources (e.g., from step 225). For example, if the highest probability of embolic source is determined to be at the left atrial appendage, step 229 may include generating a recommendation of a left atrial appendage closing procedure in order to prevent a stroke. If the embolic source is a deep vein thrombus in the legs, step 229 may include generating a recommendation of a vena cava filter that can trap the embolus before it reaches the lung, thus possibly protecting the patient from a fatal pulmonary embolism. If an ulcerating carotid plaque is the source for cerebral emboli, step 229 may include generating a recommendation of a carotid endarterctomy to attempt to eliminate the embolic source and prevent stroke.

FIGS. 3A-3C depict exemplary methods of predicting cerebral-related risks and evaluating treatment options associated with the cerebral-related risks, according to an exemplary embodiment. Emboli sources may include atheromatous plaque in a carotid artery or an aorta, heart chambers with atrial fibrillation, and/or prosthetic heart valves. The presence of microembolisms may correlate with a patient's risk of stroke, TIA, cognitive impairment, and/or postoperative cerebral ischemia. The methods of FIGS. 3A-3C may include identifying likely embolic sources, e.g., by using computational fluid dynamics (CFD) analyses or simulations applied to patient-specific images of cerebral arteries and other vasculatures. Outputs of methods in FIGS. 3A-3C may provide predictions or recommendations for reducing the risk of stroke, TIA, cognitive impairment, and/or postoperative cerebral ischemia.

FIG. 3A is a flowchart of an exemplary method 300 of determining destination(s) in cerebral vessels for an embolus dislodged from a location in patient's vasculature, according to an exemplary embodiment. The method of FIG. 3A may be performed by server systems 106, based on information, images, and data received from physicians 102 and/or third party providers 104 over electronic network 101. In one embodiment, steps 301-307 may include receiving various information relating to a patient. For example, step 301 may include receiving the patient's medical history, including any inherited or acquired hypercoagulable state that may affect thrombotic risk. For instance, patient medical history may include the patient's family medical history, as well as the patient's prior history of deep venous thrombosis or pulmonary embolism, factor V Leiden, cancer, and/or recent trauma or surgery. Step 303 may include receiving information on medications that the patient may be taking that may affect thrombotic risk. Examples of such medications may include: Aspirin, Clopidogrel, Coumadin/Warfarin, Heparin, etc.

In one embodiment, step 305 may include receiving the patient's physiologic conditions and/or a model of the patient's anatomy (e.g., including at least a portion of the patient's circulatory system). The model of the patient's anatomy may include a representation of the patient's heart, aortic arch, coronary, carotid, and cerebral arteries, and/or veins. Alternately or in addition, the model of the patient's anatomy may include a 3D mesh model (e.g., obtained via segmentation of cardiac and head CT images) and/or a patient-specific cerebral artery model combined with a generic circulatory model (e.g., of a coronary, aortic arch, etc.) based on a population average. Patient physiologic conditions may include, for example: age, sex, blood pressure/heart rate under rest/exercise conditions, physical activity (e.g., exercise intensity), sedentary time per day, obesity, etc.

In one embodiment, step 307 may include receiving one or more locations of interest in the patient's anatomy (e.g., a plaque, pathological area, location of possible vascular shedding, etc.). A location of interest may include a simulated culprit embolic source. In one embodiment, the locations of interest may be received in an electronic storage medium. Alternately or in addition, step 307 may include identifying one or more locations of interest in the patient's anatomy. For example, the locations of interest may be identified via invasive and/or noninvasive imaging (e.g., CT, MRI, IVUS, transcranial Doppler ultrasound, etc.). In one exemplary case, step 307 may include identifying the one or more locations of interest by detecting atherosclerotic plaques in the patient's vessel(s). Step 307 may further include storing identified location(s) of interest electronically (e.g., via an electronic storage medium, RAM, etc.). Information regarding a location of interest in the patient may include, for example, information on the presence and severity of atherosclerotic carotid artery disease, intracranial stenosis, cardiac disease, venous disease, and/or arterial dissection in the patient's anatomy. For instance, presence and severity of cardiac disease may include information on any heart condition(s), disorders, or irregularities a patient may have, e.g., atrial fibrillation (and left atrial appendage activity), performance of one or more prosthetic heart valves, patent foramen ovale, acute myocardial infarction, and/or left ventricular dysfunction.

In one embodiment, step 309 may include determining blood flow characteristics (e.g., using computational fluid dynamics (or approximation)) based on the patient's medical history, medications, physiologic condition(s), and/or anatomy (e.g., as received from steps 301-307). Step 309 may further include determining a circulatory destination probability of a dislodged embolus (e.g., an embolus dislodged from a location of interest, including the patient's aorta, carotid, or heart) based on the determined blood flow characteristics. In one embodiment, determining the circulatory destination probability, based on an embolus source, may include performing Lagrangian particle tracking. An exemplary computational fluid dynamics analysis for determining blood flow characteristics and circulatory destination probability, is described in the method of FIG. 3C.

In one embodiment, step 309 may further include outputting and/or storing the circulatory destination probability, e.g., to an electronic storage medium or display. In some instances, the circulatory destination probability may be stored such that the probability is associated with the location of interest, wherein the location of interest may be identified as a potential source location for an embolus. Furthermore, step 309 may include determining location vulnerable to embolism, based on the determined circulatory destination probabilities.

FIG. 3B is a flowchart of an exemplary method 310 of determining and evaluating emboli source locations in a patient's cerebral vasculature, according to an exemplary embodiment. The method of FIG. 3B may be performed by server systems 106, based on information, images, and data received from physicians 102 and/or third party providers 104 over electronic network 101.

In one embodiment, step 311 may include receiving one or more destination locations of interest in the patient's vasculature. For example, for cerebral-related risks (e.g., stroke, TIA, cognitive impairment, and/or postoperative cerebral ischemia), destination locations of interest may include cerebral arteries. In other words, emboli or microemboli presence in cerebral arteries may present risk of stroke, TIA, cognitive impairment, and/or postoperative cerebral ischemia.

In one embodiment, step 313 may include determining stored and/or computed circulatory destination probabilities associated with a received destination location (e.g., of step 309). For example, the received destination locations may be identified as locations vulnerable to embolism.

In one embodiment, step 315 may include determining source location(s) associated with a computed circulatory destination probability (e.g., of step 313), and thereby associated with a received destination location (e.g., of step 311). For example, step 315 may include retrieving stored embolic sources (e.g., from method 300), based on circulatory destination probabilities for the one or more destinations of interest. For example, an embolic source may include one or more locations of interest (e.g., from step 307).

In one embodiment, step 317 may include generating various outputs including, for example, destination/vulnerable location(s) (e.g., of step 309) and/or source location(s) (e.g., of step 315). For example, step 317 may include outputting a representation including one or more destination probabilities in the patient cerebral artery model. In one case, such a representation of the cerebral artery model may include visual indication (e.g., highlighting) at vulnerable embolism location(s) and/or at embolic source(s) associated with the patient's cerebral or vulnerable embolism location (s). In one embodiment, the output cerebral artery model may be stored in an electronic storage medium. Alternately or in addition, step 317 may include generating a representation or display showing selected embolic sources. For example, the representation or display may include a user interface for a user (e.g., a health care provider) to select one or more locations and/or embolic sources in the received model of the patient's anatomy or output cerebral artery model. The representation or display may then include numerical or color indicators showing risk of embolism or destination probabilities and/or embolic paths. For example, a representation of an embolic path may include a line indicating at least a portion of the journey of an embolus through the patient's circulatory system as it travels from a source location to a target location in the patient's vasculature. The outputs of step 317 may be made accessible to physicians evaluating potential treatments to reduce the patient's risk of stroke or TIA. For example, the treatments may include targeted action taken at the identified vulnerable locations. For example, targeted treatments may include actions that may reduce risk of stroke or TIA, including carotid endarterectomy and/or carotid stenting. In such a scenario, the carotid bifurcation may be a vulnerable location. For instance, the carotid bifurcation as an embolic source may produce symptoms of amaurosis fugax (temporary blindness in one eye) if an embolus tracks to the patient's ophthalmic artery branch from the bifurcation. The carotid bifurcation as an embolic source may produce a stroke if the embolus tracks to the middle cerebral artery from the carotid bifurcation. Another preventative treatment for embolism may include treatments for embolism to the toe, which may cause gangrene of the toe. For such cases, an embolus source may include the patient's aortic bifurcation or iliac artery and a treatment may include aortic femoral bypass surgery or iliac stenting, respectively. Additionally or alternatively, step 317 may include assessing hemodynamic and biomechanical forces acting on a patient's vessels or plaque in the patient's vessels. The forces may include sheer stress, drag, tangential pressure, etc. Such forces, as well as, e.g., the timing, duration, and magnitude of such forces, may be used to stratify risks and/or determine treatment options or recommendations. In other words, levels of risk for a patient may be evaluated as a function of various threshold levels or combinations of hemodynamic force(s) at a location in a patient's vessel, biomechanical force(s) at a location in a patient's vessel, frequency/timing of the force, and/or duration of the force. For example, a magnitude of a hemodynamic or biomechanical force on a plaque may increase a likelihood of an embolus being dislodged. In one scenario, step 317 may include estimating the likelihood of an embolus being dislodged from a patient's vessel wall, based on whether the magnitude of hemodynamic or biomechanical force at a location of plaque in the patient's vasculature exceeds a threshold magnitude of force, for a given period of time.

In one embodiment, step 319 may include analysis of the output of step 317, e.g., associating destination probabilities with various locations in the patient cerebral artery model and effects of emboli presence at the destinations. For example, step 319 may include outputting a patient risk of stroke, TIA, cognitive impairment, or postoperative cerebral ischemia associated with the computed risk of embolism at one or more locations in the patient cerebral artery model (e.g., based on the destination probability). Alternately or in addition, step 319 may include calculating and/or displaying a cumulative risk/probability (e.g., of cognitive impairment) over time. For example, step 319 may include calculating the destination probabilities over a span of time, and then outputting a predicted risk/probability based on the collective calculations (e.g., by repeating the above steps with multiple iterations to simulate the cumulative effects of an ongoing release of microemboli).

FIG. 3C is a flowchart of an exemplary method 320 of determining blood flow characteristics and circulatory destination probability of a dislodged embolus, in order to predict cerebral-related risks and evaluate treatment options associated with the cerebral-related risks, according to an exemplary embodiment. The method of FIG. 3C may be performed by server systems 106, based on information, images, and data received from physicians 102 and/or third party providers 104 over electronic network 101.

In one embodiment, step 321 may include computing a velocity field of blood flow through a portion of the patient's anatomy (e.g., the patient's heart, coronary, cerebral, carotid, and/or aortic arch). Computing the velocity field of blood flow may include solving Navier-Stokes equations computationally under the received patient physiologic conditions. For example, a computational model may include venous circulation as well as arterial circulation. Venous circulation may be modeled by including collapsibility of veins due to the effect of forces external to the body (e.g., gravity, external pressure, etc.) or forces internal to the body (e.g., intra-abdominal and/or intra-thoracic pressure from, for instance, respiration, straining, valsalva, etc.).

In one embodiment, step 323 may include simulating the path of a dislodged embolus through the patient's circulatory system based on the computed velocity field. For example, step 323 may include virtually injecting particles into the blood flow at the received or identified potential embolic sources (e.g., received or identified carotid stenosis, atheromatous plaque in aorta, and/or heart valves from step 315).

Step 325 may include determining a trajectory of one or more of the particles (e.g., by solving the ordinary differential equation of $\dot{x}(t)=u(x, t); x(t_0)=x_0$ using an appropriate numerical method, where u(x, t) is the velocity field and x(t) is the location of particle at time t). The size and number of particles may be determined by non-invasive imaging (e.g., ultrasound) or estimated by the disease severities of embolic sources.

In one embodiment, step 327 may include determining the destination probability of an embolus. For example, step 327 may include computing the ratio of the number of particles reaching the target cerebral arteries (e.g., of step 311) with respect to the total number of released particles. Alternately or in addition, step 327 may include tracking the path of a single particle traveling through the patient's circulatory system. In one embodiment, step 329 may include storing the destination probability of the embolus (e.g., to an electronic storage medium and/or RAM).

FIGS. 4A-4C depict exemplary methods of predicting peripheral-related risks and evaluating treatment options associated with the peripheral-related risks, according to an exemplary embodiment. The methods of FIGS. 4A-4C may include identifying embolic sources using CFD analysis in conjunction with patient-specific images of peripheral arteries and veins. Identifying the embolic sources in peripheral arteries and veins may help determine treatment to reduce a patient's risk of kidney embolism, pulmonary (e.g., right-sided or venous) embolism, and/or mesenteric or lower extremity embolism.

FIG. 4A is a flowchart of an exemplary method 400 of determining destination(s) in peripheral vessels for an embolus dislodged from a location in patient's vasculature, according to an exemplary embodiment. The method of FIG. 4A may be performed by server systems 106, based on information, images, and data received from physicians 102 and/or third party providers 104 over electronic network 101.

In one embodiment, steps 401-407 may include receiving various information on a patient. Steps 401 and 403 may be similar to steps 301 and 303, respectively. For example, step 401 may include receiving the patient's medical history, including any inherited or acquired hypercoagulable state that may affect thrombotic risk. For instance, patient medical history may include the patient's family medical history, as well as the patient's prior history of deep venous thrombosis or pulmonary embolism, factor V Leiden, cancer, and/or recent trauma or surgery. Step 403 may include receiving information on medications that the patient may be using that may affect thrombotic risk. Examples of such medications may include: Aspirin, Clopidogrel, Coumadin/Warfarin, Heparin, etc.

Step 405 may include receiving the patient's physiologic conditions and/or a model of the patient's anatomy (e.g., including at least a portion of the patient's circulatory system). The model of the patient's anatomy may include a representation of the patient's aortic arch, coronary, renal, mesenteric, and/or pulmonary and peripheral arteries and veins. Alternately or in addition, the model of the patient's anatomy may include a 3D mesh model (e.g., obtained via segmentation of peripheral, cardiac and/or abdominal CT images) and/or a patient-specific artery model combined with a generic circulatory model (e.g., of a coronary, aortic arch, etc.) based on a population average. Patient physiologic conditions may include, for example: age, sex, blood pressure/heart rate under rest/exercise conditions, physical activity (e.g., exercise intensity), sedentary time per day, obesity, etc.

In one embodiment, step 407 may include receiving one or more locations of interest in the patient's anatomy (e.g., a plaque, pathological area, location of possible vascular shedding, etc.). For example, the locations of interest may be received from an electronic storage medium. Alternately or in addition, step 407 may include identifying one or more locations of interest in the patient's anatomy. For example, the locations of interest may be identified via invasive and/or noninvasive imaging (e.g., CT, MRI, IVUS, Doppler ultrasound, etc.). In one exemplary case, step 407 may include identifying the one or more locations of interest by detecting atherosclerotic plaques in a patient's vessel(s). Step 407 may further include storing the identified location(s) of interest electronically (e.g., via an electronic storage medium, RAM, etc.). Information regarding a location of interest in the patient may include, for example, information on the presence and severity of atherosclerotic carotid artery disease, cardiac disease, venous disease, and/or arterial dissection in the patient's anatomy. For instance, the presence and severity of cardiac disease may include information on any heart condition(s), disorders, or irregularities a patient may have, e.g., atrial fibrillation (and/or left atrial appendage activity), performance of one or more prosthetic heart valves, patent foramen ovale, acute myocardial infarction, and/or left ventricular dysfunction.

In one embodiment, step 409 may include determining blood flow characteristics (e.g., using a computational fluid dynamics simulation and/or approximation). Step 409 may further include determining a circulatory destination probability of a dislodged embolus (e.g., an embolus dislodged from a culprit embolic source, including the patient's aorta, carotid, or heart). In one embodiment, determining the circulatory destination probability, based on an embolus source, may include performing Lagrangian particle tracking. An exemplary computational fluid dynamics analysis for determining blood flow characteristics and circulatory destination probability, is described in the method of FIG. 4C.

In one embodiment, step 409 may further include outputting and/or storing the circulatory destination probability, e.g., to an electronic storage medium or display. In some instances, the circulatory destination probability may be stored such that the probability is associated with the location of interest, wherein the location of interest may be identified as a potential culprit embolus source. Furthermore, step 409 may include determining locations vulnerable to embolism, based on the determined circulatory destination probabilities.

FIG. 4B is a flowchart of an exemplary method 410 of determining and evaluating source locations of embolism in a patient's peripheral vasculature, according to an exemplary embodiment. The method of FIG. 4B may be performed by server systems 106, based on information, images, and data received from physicians 102 and/or third party providers 104 over electronic network 101.

In one embodiment, step 411 may include receiving one or more destination locations of interest in the patient's vasculature. For example, for peripheral-related risks (e.g., kidney embolism, pulmonary (e.g., right-sided or venous) embolism, and/or mesenteric or lower extremity embolism), destination locations of interest may include one or more pulmonary, renal, peripheral, or femoral arteries. In other words, emboli presence in the pulmonary, renal, or femoral arteries may present risk of pulmonary (e.g., right-sided or venous) embolism, kidney embolism, lower extremity embolism, and/or mesenteric embolism, respectively.

In one embodiment, step 413 may include determining stored and/or computed circulatory destination probabilities associated with a received destination location (e.g., of step 409). For example, the received destination locations may be identified as locations vulnerable to embolism.

In one embodiment, step 415 may include determining source location(s) associated with a determined circulatory destination probability (e.g., of step 413), and thereby associated with a received destination location (e.g., of step 411). For example, step 415 may include retrieving stored embolic sources (e.g., from method 400), based on circulatory destination probabilities for the one or more destinations of interest. For example, an embolic source may include one or more of the one or more locations of interest (e.g., from step 407).

In one embodiment, step 417 may include generating various outputs including, for example, destination/vulnerable location(s) (e.g., of step 411) and/or source location(s) (e.g., of step 415). For example, step 417 may include outputting a representation including one or more destination probabilities and/or embolic paths in a patient artery model. In one case, such a representation of the artery model may include visual indication (e.g., highlighting) at vulnerable embolism location(s) and/or at embolic source(s) associated with the patient's vulnerable embolism location(s). In one embodiment, the representation including the artery model may be stored to an electronic storage medium. Alternately or in addition, step 417 may include generating a representation or display showing selected location(s) of embolic sources.

For example, the representation or display may include a user interface for a user (e.g., a health care provider) to select one or more locations and/or embolic sources in the received model of the patient's artery model or the representation of the artery model. The representation or display may then include numerical or color indicators showing risk of embolism or destination probabilities. The outputs of step 417 may be made accessible to physicians evaluating potential treatments to reduce the risk or number of pulmonary, kidney, mesenteric, or lower extremity embolisms.

In one embodiment, step 419 may include analysis of the output of step 417, e.g., associating destination probabilities with various locations in the patient artery model and effects of emboli presence at the destinations. For example, step 419 may include outputting a patient risk of pulmonary, kidney, mesenteric, or lower extremity embolisms, based on the computed risk of embolism at one or more locations in the patient artery model.

FIG. 4C is a flowchart of an exemplary method 420 of determining blood flow characteristics and circulatory destination probability of a dislodged embolus for peripheral-related risks, according to an exemplary embodiment. The method of FIG. 4C may be performed by server systems 106, based on information, images, and data received from physicians 102 and/or third party providers 104 over electronic network 101.

In one embodiment, step 421 may include computing a velocity field of blood flow in the patient's anatomy (e.g., the patient's heart, coronary, cerebral, carotid, and aortic arch). Computing the velocity field of blood flow may include computationally solving Navier-Stokes equations under the received patient physiologic conditions. For example, a computational model may include venous circulation as well as arterial circulation. Venous circulation may be modeled by including collapsibility of veins due to the effect of external forces (e.g., gravity, external pressure, etc.).

In one embodiment, step 423 may include simulating the path of a dislodged embolus through the patient's circulatory system based on the computed velocity field. For example, step 423 may include may include injecting particles virtually in the received or identified potential embolic sources (e.g., received or identified femoral veins, atheromatous plaque in aorta, and/or heart valves from step 415).

Step 425 may include determining a trajectory of particles (e.g., by solving the ordinary differential equation of $\dot{x}(t)=u(x, t)$; $x(t_0)=x_0$ using an appropriate numerical method, where $u(x, t)$ is the velocity field and $x(t)$ is the location of particle at time t). The size and number of particles may be determined by non-invasive imaging (e.g., ultrasound) or estimated by the disease severities of embolic sources.

Step 427 may include determining the destination probability of an embolus (e.g., by computing the ratio of the number of particles reaching target pulmonary, renal, or femoral arteries (e.g., of step 411) with respect to the total number of released particles). Step 429 may include storing the destination probability of the embolus (e.g., to an electronic storage medium and/or RAM).

FIG. 5A is a flowchart of an exemplary method 500 of assessing or assigning a risk of potential emboli dislodgement associated with an invasive procedure, according to an exemplary embodiment. The method of FIG. 5A may be performed by server systems 106, based on information, images, and data received from physicians 102 and/or third party providers 104 over electronic network 101. FIGS. 5A-5C may include evaluating a risk of embolism that may be associated with one or more invasive procedures. Emboli may be dislodged during invasive procedures, including endovascular procedures (e.g., angiography, stenting procedures, transcatheter valve procedures (e.g., transcatheter aortic valve implantation (TAVI)), and/or revascularization of coronary, carotid, and/or peripheral arteries. For example, method 500 may include providing a probability of emboli dislodgement from potential embolic sources, along the trajectory of invasive procedures.

In one embodiment, steps 501-507A may include receiving various information on a patient. Steps 501 may be similar to steps 301 and 401, and step 503 may be similar to steps 303 and 403. For example, step 501 may include receiving the patient's medical history, including any inherited or acquired hypercoagulable state that may affect thrombotic risk. For instance, patient medical history may include the patient's family medical history, as well as the patient's prior history of deep venous thrombosis or pulmonary embolism, factor V Leiden, cancer, and/or recent trauma or surgery. Step 503 may include receiving information on medications that the patient may be using that may affect thrombotic risk. Examples of such medications may include: Aspirin, Clopidogrel, Coumadin/Warfarin, Heparin, etc.

In one embodiment, step 505 may include receiving the patient's physiologic conditions and/or a model of the patient's anatomy (e.g., including at least a portion of the patient's circulatory system). The model of the patient's anatomy may include a representation of the patient's aortic arch, coronary, carotid, and/or cerebral arteries and veins. Alternately or in addition, the model of the patient's anatomy may include a 3D mesh model (e.g., obtained via segmentation of cardiac and/or head CT images) and/or a patient-specific artery model combined with a generic circulatory model (e.g., of a coronary, aortic arch, etc.) based on a population average. Patient physiologic conditions may include, for example: age, sex, blood pressure/heart rate under rest/exercise conditions, physical activity (e.g., exercise intensity), sedentary time per day, obesity, etc. Further data on patient information or modeling the patient's anatomy/physical state may include any data on extrinsic forces and/or conditions that may act on an area of interest of the patient's body, including body position (e.g., supine, standing, standing on head, flexion, extension, etc.) and/or extreme conditions (e.g., acceleration or deceleration, sporting conditions, g-forces, deep diving, valsalva, shoveling snow, pregnancy, etc.). Any extrinsic forces that may affect the circulatory system may be taken into account for step 505, since any of these factors may be a triggering event for an embolus.

In one embodiment, step 507A may include receiving one or more locations of interest in the patient's anatomy (e.g., a plaque, pathological area, location of possible vascular shedding, etc.). For example, the locations of interest may be received from an electronic storage medium. Alternately or in addition, step 507A may include identifying one or more locations of interest in the patient's anatomy. For example, the locations of interest may be identified via invasive and/or noninvasive imaging (e.g., CT, MRI, IVUS, Doppler ultrasound, etc.). In one exemplary case, step 507A may include identifying the one or more locations of interest by detecting atherosclerotic plaques in a patient's vessel(s). Identified location(s) of interest may be stored electronically (e.g., via an electronic storage medium, RAM, etc.). Information about a location of interest in the patient may include, for example, information on the presence and/or severity of atherosclerotic carotid artery disease, intracranial stenosis, cardiac disease, venous disease, and/or arterial dissection in the patient's anatomy. For instance, presence and severity of cardiac disease may include information on any heart condition(s), disorder(s), or irregularities a patient may have, e.g., atrial fibrillation (and/or left atrial appendage activity), performance of one or more prosthetic heart valves, patent foramen ovale, acute myocardial infarction, and/or left ventricular dysfunction.

In one embodiment, step 507B may include determining a potential trajectory of an invasive procedure in the model of the patient's anatomy. The potential trajectory may be determined, based on the one or more received and/or identified locations of interest (of step 507A). Exemplary trajectories may include guide-wire, catheter, or pressure wire trajectories along a superficial femoral artery, aortic arch, etc.

In one embodiment, step 509 may include determining blood flow characteristics (e.g., using computational fluid dynamics (or approximation)). Step 509 may further include determining a circulatory destination probability of a dislodged embolus, e.g., an embolus dislodged from a culprit embolic source along the trajectory of the invasive procedure (e.g., from step 507B). In one embodiment, determining the circulatory destination probability, based on an embolus source, may include performing Lagrangian particle tracking. An exemplary computational fluid dynamics analysis for determining blood flow characteristics and circulatory destination probability is described in the method of FIG. 5C.

In one embodiment, step 509 may further include outputting and/or storing the circulatory destination probability, e.g., to an electronic storage medium or display. In some instances, the circulatory destination probability may be stored such that the probability is associated with the location of interest, wherein the location of interest may be identified as a potential source location for an embolus. Furthermore, step 509 may include determining locations vulnerable to embolism, based on the determined circulatory destination probabilities.

FIG. 5B is a block diagram of an exemplary method 510 of determining and evaluating source locations of embolism associated with invasive procedures, according to an exemplary embodiment. The method of FIG. 5B may be performed by server systems 106, based on information, images, and data received from physicians 102 and/or third party providers 104 over electronic network 101.

In one embodiment, step 511 may include receiving one or more destination locations of interest in the patient's vasculature. For example, destination locations of interest for cerebral-related risks (e.g., stroke, TIA, cognitive impairment, or postoperative cerebral ischemia) may include one or more cerebral arteries. For peripheral-related risks (e.g., kidney embolism, pulmonary (e.g., right-sided or venous) embolism, and/or mesenteric or lower extremity embolism), destination locations of interest may include one or more pulmonary, renal, peripheral, or femoral arteries.

In one embodiment, step 513 may include determining stored and/or computed circulatory destination probabilities associated with a received destination location (e.g., of step 509). For example, the received destination locations may be identified as locations vulnerable to embolism.

In one embodiment, step 515 may include determining source location(s) associated with a computed circulatory destination probability (e.g., of step 513), and thereby associated with a received destination location (e.g., of step 515). For example, step 515 may include retrieving stored embolic sources (e.g., from method 500), based on circulatory destination probabilities for the one or more destinations of interest. For example, an embolic source may include one or more of the one or more locations of interest (e.g., from step 507A). In one embodiment, step 515 may involve determining associations between the computed destination probabilities and embolic sources located along a trajectory of the invasive procedure (e.g., from step 507B). For example, step 515 may include finding or identifying, of the embolic sources associated with the computed destination probabilities from step 509, a subset of embolic sources that may be located along one or more trajectories of the invasive procedure from step 507B.

In one embodiment, step 517 may include generating various outputs including, for example, destination/vulnerable location(s) (e.g., of step 509) and/or source location(s) (e.g., of step 515). For example, step 517 may include outputting a representation including one or more destination probabilities in a patient artery model. In one case, such a representation of the artery model may include a visual indication (e.g., highlighting) at one or more trajectories of an invasive procedure, at vulnerable embolism location(s), at possible locations along an embolus's path through the patient's circulatory system, and/or at embolic source(s) associated with the patient's cerebral or vulnerable embolism location(s). In one embodiment, the representation including the artery model may be stored to an electronic storage medium. Alternately or in addition, step 517 may include generating a representation or display showing selected location(s) of embolic sources.

For example, the representation or display may include a user interface for a user (e.g., a health care provider) to compare the efficacy of one or more potential treatments in reducing risk associated with invasive procedures. The representation or display may then include numerical or color indicators showing risk of embolism or destination probabilities. The outputs of step 517 may be made accessible to physicians evaluating potential treatments to reduce the risk or number of embolisms resulting from invasive procedures.

In one embodiment, step 519 may include analysis of the output of step 517, e.g., associating destination probabilities with various locations in the patient artery model and effects of emboli presence at the destinations. For example, step 519 may include outputting a patient risk of emboli dislodgement and/or harmful emboli dislodgement that may occur as a result of an invasive procedure performed on the patient's vasculature. Alternately or in addition, step 519 may include outputting a patient risk of embolism(s) and/or harmful embolism(s) that may occur as a result of an invasive procedure performed on the patient's vasculature. Step 519 may include generating a recommendation regarding the one or more potential treatments for reducing risk associated with invasive procedures.

FIG. 5C is a flowchart of an exemplary method 520 of determining blood flow characteristics and circulatory destination probability of a dislodged embolus related to invasive procedures, according to an exemplary embodiment. The method of FIG. 5C may be performed by server systems 106, based on information, images, and data received from physicians 102 and/or third party providers 104 over electronic network 101.

In one embodiment, step 521 may include computing a velocity field of blood flow in the patient's anatomy (e.g., the patient's heart, coronary, cerebral, carotid, renal, femoral, and/or aortic arch). Computing the velocity field of blood flow may include computationally solving Navier-Stokes equations under the received patient physiologic conditions. For example, a computational model may include venous circulation as well as arterial circulation. Venous circulation may be modeled by including collapsibility of veins due to the effect of external forces (e.g., gravity, external pressure, etc.).

In one embodiment, step 523 may include simulating the path of a dislodged embolus through the patient's circulatory system based on the computed velocity field. For example, step 523 may include injecting particles virtually in the received or identified potential embolic sources (e.g., received or identified carotid stenosis, atheromatous plaque in aorta, heart valves, etc. from step 515).

In one embodiment, step 525 may include determining the trajectory of particles (e.g., by solving the ordinary differential equation of $\dot{x}(t)=u(x, t); x(t_0)=x_0$ using an appropriate numerical method, where $u(x, t)$ is the velocity field and $x(t)$ is the location of particle at time t). The size and number of particles may be determined by non-invasive imaging (e.g., ultrasound) or estimated by the disease severities of embolic sources.

In one embodiment, step 527 may include determining the destination probability of an embolus (e.g., by computing the ratio of the number of particles reaching the target cerebral or peripheral arteries with respect to the total number of released particles). Step 529 may include storing the probability of the destination (e.g., to an electronic storage medium and/or RAM).

Embolisms may form from emboli originating from various sources in a patient's vasculature and various factors contributing to the patient's blood flow. The present disclosure includes systems and methods for predicting embolisms based on a circulatory destination probability of an embolus traveling through a patient's bloodstream. At the same time, the systems and methods provide determinations of the level of harm introduced by an embolism traveling through a patient's bloodstream. Accordingly, the disclosed systems and methods may provide patient risk assessments and treatment plans related to embolisms, based on circulatory destination probabilities of emboli.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of determining a patient risk assessment or treatment plan based on emboli dislodgement and destination, the method comprising:
   receiving a patient-specific anatomic model generated from patient-specific imaging of at least a portion of a patient's vasculature;
   determining or receiving a plurality of source locations of interest in the patient-specific anatomic model of the patient's vasculature, where each source location of interest is associated with an identified plaque, pathological area, or location of vascular shedding in the patient's vasculature;
   determining or receiving a destination location of interest in the patient-specific anatomic model of the patient's vasculature;
   determining a patient-specific probability of an embolus lodging at the destination location of interest; and
   determining, based on the plurality of source locations of interest, a vascular source location of the embolus in the patient's vasculature, based on the determined patient-specific probability.

2. The computer-implemented method of claim 1, further comprising:
   determining, in the patient's vasculature, a location of a plaque, a location meeting a predetermined criteria of pathology, or a location of possible vascular shedding; and
   determining or receiving the source location of interest in the patient-specific anatomic model based on the determined location of plaque, determined location meeting the predetermined criteria of pathology, or the location of possible vascular shedding.

3. The computer-implemented method of claim 1, further comprising:
   determining a target location in the patient's vasculature, wherein the determined patient-specific probability is a probability that the embolus traveling through the patient's vasculature reaches the target location.

4. The computer-implemented method of claim 1, further comprising:
   determining the destination location of interest based on the determined patient-specific probability.

5. The computer-implemented method of claim 1, further comprising:
   determining an association between a target location in the patient-specific anatomic model, the determined patient-specific probability, and the source location of interest; and
   outputting a patient risk assessment or treatment plan based on the determined association.

6. The computer-implemented method of claim 5, further comprising:
   determining, for a second source location of interest, a second patient-specific probability of an embolus associated with the second source location of interest;
   determining an association between the target location in the patient-specific anatomic model, the determined patient-specific probability, and the second source location of interest;

comparing the association between the target location in the patient-specific anatomic model, the determined patient-specific probability, and the source location of interest, and the association between the target location in the patient-specific anatomic model, the determined patient-specific probability, and the second source location of interest; and determining or generating a display or a treatment recommendation based on the comparing.

7. The computer-implemented method of claim 1, further comprising:

determining patient risk of a disease, based on the determined patient-specific probability of the embolus, wherein the patient risk of the disease includes patient risk of a disease associated with a location in the patient's vasculature.

8. The computer-implemented method of claim 1, further comprising:

simulating a path of a dislodged embolus from each source location of interest, wherein the determined patient-specific probability of an embolus lodging at the destination location of interest is based on the simulated path.

9. A computer system for determining a patient risk assessment or treatment plan based on emboli dislodgement and destination, the system comprising:

at least one data storage device storing instructions for the determining a patient risk assessment or treatment plan based on emboli dislodgement and destination; and at least one processor configured to execute the instructions to perform a method including:

receiving a patient-specific anatomic model generated from patient-specific imaging of at least a portion of a patient's vasculature;

determining or receiving a plurality of source locations of interest in the patient-specific anatomic model of the patient's vasculature, where each source location of interest is associated with an identified plaque, pathological area, or location of vascular shedding in the patient's vasculature;

determining or receiving a destination location of interest in the patient-specific anatomic model of the patient's vasculature;

determining a patient-specific probability of an embolus lodging at the destination location of interest; and determining, based on the plurality of source locations of interest, a vascular source location of the embolus in the patient's vasculature, based on the determined patient-specific probability.

10. The system of claim 9, wherein the system is further configured for:

determining, in the patient's vasculature, a location of a plaque, a location meeting a predetermined criteria of pathology, or a location of possible vascular shedding; and determining or receiving the source location of interest in the patient-specific anatomic model based on the determined location of plaque, determined location meeting the predetermined criteria of pathology, or the location of possible vascular shedding.

11. The system of claim 9, wherein the system is further configured for:

determining a target location in the patient's vasculature, wherein the determined patient-specific probability is a probability that the embolus traveling through the patient's vasculature reaches the target location.

12. The system of claim 9, wherein the system is further configured for:

determining the destination location of interest based on the determined patient-specific probability.

13. The system of claim 9, wherein the system is further configured for:

determining an association between a target location in the patient-specific anatomic model, the determined patient-specific probability, and the source location of interest; and outputting a patient risk assessment or treatment plan based on the determined association.

14. The system of claim 13, wherein the system is further configured for:

determining, for a second source location of interest, a second patient-specific probability of an embolus associated with the second source location of interest;

determining an association between the target location in the patient-specific anatomic model, the determined patient-specific probability, and the second source location of interest;

comparing the association between the target location in the patient-specific anatomic model, the determined patient-specific probability, and the source location of interest, and the association between the target location in the patient-specific anatomic model, the determined patient-specific probability, and the second source location of interest; and determining or generating a display or a treatment recommendation based on the comparing.

15. The system of claim 9, wherein the system is further configured for:

determining patient risk of a disease, based on the determined patient-specific probability of the embolus, wherein the patient risk of the disease includes patient risk of a disease associated with a location in the patient's vasculature.

16. The system of claim 9, the system is further configured for:

simulating a path of a dislodged embolus from each source location of interest, wherein the determined patient-specific probability of an embolus lodging at the destination location of interest is based on the simulated path.

17. A non-transitory computer readable medium for use on a computer system containing computer-executable programming instructions for performing a method of determining a patient risk assessment or treatment plan based on emboli dislodgement and destination, the method comprising:

receiving a patient-specific anatomic model generated from patient-specific imaging of at least a portion of a patient's vasculature;

determining or receiving a plurality of source locations of interest in the patient-specific anatomic model of the patient's vasculature, where each source location of interest is associated with an identified plaque, pathological area, or location of vascular shedding in the patient's vasculature;

determining or receiving a destination location of interest in the patient-specific anatomic model of the patient's vasculature;

determining a patient-specific probability of an embolus lodging at the destination location of interest; and determining, based on the plurality of source locations of interest, a vascular source location of the embolus in the patient's vasculature, based on the determined patient-specific probability.

18. The non-transitory computer readable medium of claim 17, the method further comprising:
   determining, in the patient's vasculature, a location of a plaque, a location meeting a predetermined criteria of pathology, or a location of possible vascular shedding; and
   determining or receiving the source location of interest in the patient-specific anatomic model based on the determined location of plaque, determined location meeting the predetermined criteria of pathology, or the location of possible vascular shedding.

19. The non-transitory computer readable medium of claim 17, the method further comprising:
   determining a target location in the patient's vasculature, wherein the determined patient-specific probability is a probability that the embolus traveling through the patient's vasculature reaches the target location.

20. The non-transitory computer readable medium of claim 19, the method further comprising:
   determining the destination location of interest based on the computed determined patient-specific probability.

\* \* \* \* \*